United States Patent [19]

Bushick

[11] 4,013,705
[45] Mar. 22, 1977

[54] AMMOXIDATION PROCESS FOR MAKING DICYANONAPHTHALENE
[75] Inventor: Ronald D. Bushick, Glen Mills, Pa.
[73] Assignee: Suntech, Inc., St. Davids, Pa.
[22] Filed: Mar. 9, 1976
[21] Appl. No.: 665,342
[52] U.S. Cl. .............................. 260/465 C; 252/474
[51] Int. Cl.² .............. C07C 120/14; C07C 121/62
[58] Field of Search ............................... 260/465 C
[56] References Cited
UNITED STATES PATENTS
3,959,336   5/1976   Bushick et al. ................ 260/465 C Primary Examiner—Dolph H. Torrence
Attorney, Agent, or Firm—J. Edward Hess; Donald R. Johnson; Paul Lipsitz

[57] ABSTRACT

In the process of making dicyanonaphthalene by reacting a di-lower alkylnaphthalene, ammonia and oxygen under ammoxidation conditions, the improvement which comprises carrying out said ammoxidation in the presence of a supported alkali-metal vanadium bronze catalyst, promoted with iron and with a molar ratio of ammonia to dialkylnaphthalene of from at least about 10:1 to about 30:1. The invention also embodies the iron promoted catalyst.

12 Claims, No Drawings

AMMOXIDATION PROCESS FOR MAKING DICYANONAPHTHALENE

It is known in the art to effect ammoxidation of aromatic hydrocarbons such as alkylated benzenes and naphthalenes with ammonia and oxygen to obtain the corresponding nitriles. Wide reaction conditions and numerous types of catalysts have been employed for such reactions including vanadium oxides either alone or promoted with one or more different metals. In British Pat. No. 977,755 it is disclosed that alkylated compounds generally, but particularly those of the benzene series (e.g., toluene, the xylenes, etc.) and alkyl-substituted pyridines may be converted to the corresponding nitriles by ammoxidation using 3 to 10 times the stoichiometric ratio of ammonia to hydrocarbon and employing as catalyst an oxygen containing compound with or without promoters such as oxides of titanium, iron, vanadium and others.

In British Pat. No. 1,319,287 an ammoxidation process for alkylated benzene hydrocarbons is disclosed using as catalyst a mixture of vanadium oxide and molybdenum oxide and the mole ratio of ammonia to hydrocarbon is given desirably as 4 to 14 with the comment that "little sense lies in employing more than 12 moles of ammonia per mole of hydrocarbon, since an increase in yield cannot be obtained thereby."

In U.S. Pat. No. 3,433,823 ammoxidation of methyl aromatic compounds such as toluene, xylene, methylnaphthalene, 1,4-dimethylnaphthalene, and the like is disclosed using as catalyst a mixture of a vanadium polyphosphate and an oxide of molybdenum, copper, tungsten, thorium, uranium or zirconium and where the ammonia to hydrocarbon mole ratio is given as 0.2 to 20, preferably 1 to 10.

The numerous disclosures in the prior art of ammoxidation such as those given above generally consider the alkylated benzenes and alkylated naphthalenes to be equivalent in their reaction with ammonia and oxygen. However, experimental work has shown that in the case of 2,6-dimethylnaphthalene the reaction parameters of the prior art do not enable ammoxidation to be achieved in a manner suitable for an economically viable process. For example, with prior art conditions, the 2,6-dicyanonaphthalene is obtained with rather low selectively which makes the process of low commercial merit.

In accord with the process of this invention a di-lower alkyl (e.g., $C_1$ to $C_4$) naphthalene (such as 2,4- and 2,6-dicyanonaphthalene) is obtained with very high selectivity (on the order of about 90% or higher) by reacting the dialkylnaphthalene, ammonia, and oxygen under ammoxidation conditions and in the presence of a supported alkali-metal-vanadium bronze catalyst promoted with an iron compound and employing a mole ratio of ammonia to dialkylnaphthalene of from at least about 10:1 to about 30:1. The ratio of ammonia to hydrocarbon reactant is preferably varied with the pressure at which the reaction will be carried out. When atmospheric pressure or a pressure of about 5 to 10 psig. is used, the ratio used will preferably be about 15:1. When the reaction pressure is 30 to 50 psig., then a ratio of about 25 to 30 will preferably be employed. By using such ratios the maximum selectivity to nitrile product will be achieved.

The process of the invention is carried out in either a fixed or fluidized bed of operation at a temperature between about 375° C. and 550° C., preferably from about 400° to about 450° C., at atmospheric pressure, or higher; say up to about 100 psig. although about 75 psig. (about 5 atm) is the preferred upper limit. The source of oxygen is preferably air, but any oxygen source is suitable. The process enables rather limited amounts of oxygen to be used and this, in turn, is favorable in that less burn of hydrocarbon reactant occurs. Thus, the mole ratio of oxygen to hydrocarbon in the reactant stream will usually be stoichiometric (3:1) or less and it is preferable to use from about 2.5:1 to about 3.0:1. The ratio of ammonia to hydrocarbon used in the process of the invention is critical for obtaining high nitrile selectivity and will be at least about 10:1 and the upper ratio will be about 30:1.

It will be understood that the contact time for the reactants over the catalyst will vary over a wide range, but will usually be from about 0.1 to 30 seconds preferably about 1 to 10 seconds. The contact time actually used will depend upon catalyst loading, catalyst volume, temperature and other parameters, and the skilled art worker will have no difficulty in selecting an appropriate contact time dependent upon these reaction parameters.

The reactant feed stream, will, of course, contain other materials, as for example, the inert ingredients of air, recycled 2,6-dimethylnaphthalene, and other products associated with the recycle stream. This use of a recycle stream will make possible a still more efficient process.

In addition to the above required parameters of the process it is essential that a particular type of catalyst be used. It is known in the art that the addition of an alkali-metal compound to vanadium pentoxide will, when the mixture is heated yield complex materials with anomalous valencies known as a vanadium bronzes. Such lithium bronzes are discussed by Volkov et al, Zh. Neorg. Khim: 17 (6): 1529–1532 (1972). Vanadium bronzes with sodium are described by Pouchard et al., Bull de la Soc. Chimique de France, No. 7, pages 274,245 (1968), and No. 11 pages 43434348 (1967). Similarly, potassium containing vanadium bronzes are discussed by Holtzberg et al., J. Am Chem, Soc. Vol. 78, pages 1536–40 (1956). Lithium bronzes are described by Hardy et.al., Bull de la Soc. Chimique de France, No. 4, 1056–65 (1965) and by Reisman et al. Jour. Physical Chemistry 66 1181–85 (1962). Also of interest is the article by P. Hagenmuller entitled "Tungsten Bronzes, Comprehensive Inorganic Chemistry" edited by J. S. Bailar, Jr. et al. and published in 1973 by Pergamon Press.

These bronze materials are prepared by mixing an appropriate alkali-metal compound (e.g., carbonate, oxalate, etc.) with vanadium pentoxide and heating the mixture at an elevated temperature for several hours. Depending upon the amount of alkali metal ion added certain phases will be established in accordance with the particular phase diagram pertinent to the mixture. Thus, for example, the Holtzberg et al. article referred to above describes the potassium bronze system and the sodium system is shown in the article by Slobodin et al., J. Appl. Chem., (USSR) Vol. 38, pp 799,803 (April 1965). Of the above alkali metal vanadium bronzes, all of which may be used in the process of the invention, the preferred bronzes for use as catalysts are the sodium bronzes and mixtures of the various species also may be employed. Preferred species include Bronze I (Bz I) which has an atomic ratio of sodium to vanadium of 0.167, Bronze II (BZ II) where the atomic ratio is 0.417, and an alpha prime phase ($\alpha$-phase) where the atomic ratio is 0.50. The terms Bronze I and Bronze II are used herein because these compounds correspond to the compounds called "first BRONZE" and "second BRONZE" by Slobovin and Fotiev, Jour. Applied Chemistry (USSR) 38 Vol. 4 pg. 799 April 1965 where the first bronze is characterized by having 14.3 mole percent of $Na_2O$ in its composition (as does BZ I) and the second bronze has 29.4 mole percent of $Na_2O$ (as does BZ II). These preferred Bronze I and $\alpha'$-phase bronzes may be further characterized by the generic empirical formula $Na_xV_2O_5$ where $x$ is greater than zero and equal to or less than 1. Other bronze systems of the $Na_xV_2O_5$ species are known where $x$ is greater than 1 and these are useful in the process, but are somewhat unstable and therefore not preferred. The BZ I species may be considered as $Na_2O \cdot V_2O_4 \cdot 5V_2O_5$ or $Na_{0.33}$ which is shown together with related members of the series at pages 573 to 575 of the Hagenmuller article as $\alpha$-$Na_xV_2O_5$ where $x$ varies from 0.22 to 0.40, the "$\beta$" designation indicating the particular crystal phase as structure of the compound. The BZ II species may be considered as $5Na_2O \cdot V_2O_4 \cdot 11V_2O_5$ or as $Na_{1+x}V_3O_8$ ($x = 0.25$) which is isotypic with $Li_{1+x}V_3O_8$ and is shown at pages 584 of the Hagenmuller article mentioned above. The $\alpha'$-phase is characterized as $Na_xV_2O_5$ where $x = 017$ to 1.0 (see page 577 of the Hagenmuller article). Also characteristic of the bronzes are their X-ray diffraction patterns wherein the strongest lines are as follows:

BZ I: 9.6, 7.3, 4.75, 3.87, 3.47, 3.38, 3.21, 3.11, 3.08, 2.92, 2.90, 2.727, 2.55, 2.45, 2.38, 2.18, 1.97, 1.87, 2.803, 1.74, 1.535, 1.492.

BZ II: 6.9, 7.04, 5.81, 3.87, 3.62, 3.50, 3.45, 3.21, 3.10, 3.67, 2.57, 2.43, 2.32, 2.27, 2.02, 1.97, 1.96, 1.81, 1.72, 1.86, 1.504, 1.333, 1.39.

$\alpha'$-phase: 11.3, 5.645, 4.82, 4.436, 3.667, 3.456, 2.967, 2.889, 2.799, 2.604, 2.436, 2.412, 2.291, 2.0196, 1.889, 1.803, 1.77, 1.689, 1.635, 1.592, 1.479.

The $\alpha'$-prime phase as with the other bronzes may be obtained by the methods described in the literature and placed on the support for use in the process, or it may be made in situ. This is readily achieved by treating the BZ II on the support with a reducing atmosphere (e.g., ammonia) or a stream similar to the hydrocarbon, ammonia and oxygen; e.g., an oxygen to hydrocarbon mole ratio of less than about 3.0.

As indicated the catalyst bronzes may comprise a mixture of the above discussed bronzes and preferred catalysts will comprise a mixture predominant in either BZ II or the $\alpha'$-prime phase or both. While BZ I used above is operable, it is preferred in order to keep the carbon oxides to a minimum to avoid having a predominant amount of BZ I in the catalyst composition.

In order to obtain the iron promoted catalyst used in the invention, an appropriate iron compound is simply added during the catalyst preparation. Preferably, an iron oxide such as $Fe_2O_3$ will be employed as the promoter. In one technique $Fe_2O_3$ is added to all of the powdered catalyst ingredients and physically mixed and the mixture pressed into pellets for use. In another technique, a water soluble iron salt (e.g., iron oxalate) is added and used with the other catalyst ingredients to impregnate the support. The amount of iron loading on the total catalyst will be from about 0.5% to about 25 mole percent (as $Fe_2O_3$) of the catalyst expressed as oxides (e.g., $V_2O_5$ plus $Na_2O$ plus $Fe_2O_3$), and from about 0.5 to about 15% as iron oxide is preferred.

The catalyst support used in the process of the invention will be comprised of $\alpha$-alumina. $\alpha$-alumina is well known in art and is exemplified by natural corundum and by the synthetic varieties which are commercially available. These materials have a high density (on the order of about 0.75 to 1.0 gm/cc.) and very low surface area (on the order of $6m^2$/gm or less). Generally the $\alpha$-alumina will contain enough sodium ions so that the sodium bronzes may be made without any addition of sodium or other alkali metal compounds. But if insufficient sodium is present, enough may be added to give the desired bronze. In making the supported catalyst all that is required is to make an aqueous slurry of powdered (170 mesh or finer) $\alpha$-alumina, alkali metal salt (preferably carbonate) and $V_2O_5$, evaporate off the water, pelletize and calcine the pellets at about 500°–600° C. for several hours, while passing a slow flow of air through the furnace. Alternatively, and preferably, the catalyst may be placed on the support by an impregnation technique where an aqueous vanadium oxalate solution containing the appropriate amount of alkali metal is deposited onto the $\alpha$-alumina support, which method is well known in the art.

As pointed out above, in making the catalyst, alkali metal ions (usually in the form of the carbonate) are added to ensure that a bronze is formed. In a particularly preferred catalyst system where a sodium-vanadium bronze is desired, the amount of sodium ion employed to make the catalsyt will be at a ratio of sodium to vanadium of 0.30 and such catalyst appears to be of high bronze purity devoid of extraneous materials which might degrade catalyst performance.

As indicated, the catalyst support will be comprised of $\alpha$-alumina but may contain other components such as silica and other metal oxides as well as the normal contaminants found in $\alpha$-alumina. However, at least about 75% by weight of the support will be $\alpha$-alumina.

The amount of catalyst on the support (e.g., catalyst loading) will be from about 0.5 to about 20% by weight, preferably about 3 to about 8%. The surface area of the catalysts used in the process is generally quite low being less than $10m^2$/gm and usually 1 to $5m^2$/gm. Pore volume of the catalyst is such that the major proportion of the pores have diameters less than about 1 micron, being on the order of about 0.2 to 1.0 micron.

After the iron promoted BZ I or a promoted mixed BZ I and BZ II catalyst is prepared, but before its use, it is preferred to age the catalyst by a heat treatment at about 500° to about 750° C. for 3 to 4 hours in order to convert most, if not all of the BZ I to the preferred BZ II.

The catalyst composition of the invention is thus an alkali metal vanadium bronze promoted with iron and is preferably a promoted Bronze II or $\alpha$-prime phase. The catalysts are preferably pelletized for use, but may also be employed in powder form.

The ammoxidation is carried out preferably in conventional apparatus, the reaction gases passing over the catalyst at reaction temperature and the effluent gases separated into the appropriate product and by-product streams. Particular advantages of the process of the invention reside in (a) low formation of carbon oxides, (b) very high selectivity for formation of dinitriles, (c) low oxygen to hydrocarbon ratios, (d) dealkylation is minimized and (e) a relatively low ammonia to hydrocarbon ratio may be used. In order to further describe and illustrate the invention the following examples employing 2,6-dimethylnaphthalene as the hydrocarbon are given:

PREPARATION OF CATALYSTS

Method A

The α-alumina support is ground into a fine powder having a particle size of about 170 mesh or less and the appropriate amount of $Fe_2O_3$ and $V_2O_5$ added to it. If analysis shows that the amount of alkali metal in the α-alumina is insufficient the desired amount sodium carbonate or other alkali metal salt is added. The mixture is then ground dry and then water is added and the mixture further agitated to make a slurry; the slurry is poured into a evaporating dish and evaporated to dryness. The dry residue is mixed further to break up agglomerates and water added to make a paste which is formed into pellets are then calcined at 540° C. for about 4 hours while air at the rate of 2.5 l/min is passed through the furnace. After cooling the catalyst pellets are ready for use.

Method B

Granulated alumina (8 – 16 mesh) is heated at 1300° C. for 4 hours. Ferric oxalate and vanadium pentoxide are suspended in 5 parts of water, heated to 80° C., and oxalic acid is added slowly to obtain a blue-colored vanadium oxalate solution. Sodium carbonate is added and the alumina is also placed in the solution. The mixture is dried over a water bath with agitation. While air is pumped in, it is indurated in a furnace at 400° C. for 16 hours to obtain the catalyst ready for use after cooling.

EXPERIMENTAL PROCEDURES

An appropriate quantity of catalyst (with or without inert diluent, e.g., quartz) is placed in a fixed bed quartz reactor (1 ¼ inches in diameter and 24 inches long). Inert packing above the catalyst serves as a preheater section and a small amount (about 1–2 inches) of similar inert packing is placed in the bottom of the reactor to support the catalyst in the reaction zone. The upper end of the reactor is equipped with an assembly having multiple openings through which the hydrocarbon, ammonia, and air (or oxygen-helium or oxygen-nitrogen mixtures) can be metered. The reactants can be mixed in this "mixing chamber" or premixed and then fed into the reactor which is operated at essentially atmospheric pressure. The rate of gas flow is adjusted so as to produce the desired contact time at a given reaction temperature over a given volume of catalyst.

The effluent gases are passed from the reactor into a chilled flask where the products were collected along with ammonium carbonate and water. The remaining escaping gas is passed through a cold water cooled condenser, a drying tube, an ascarite tube, and finally captured in a large polyvinylchloride bag.

The analysis of the organic layer, water layer, gas sample from the bag, and the weight increase of the ascarite tube (due to $CO_2$ not bound up as ammonium carbonate) enables calculation of the results (i.e., conversion, carbon balance, yield, etc.).

EXAMPLES 1–7

Using the above described procedure a catalyst of a sodium-vanadium bronze (BZ II) on α-alumina containing $Fe_2O_3$ is prepared. The data shown in Table I indicates the parameters of the process and the data which is obtained.

TABLE I

AMMOXIDATION OF 2,6-DIMETHYLNAPHTHALENE (DMN) WITH A BRONZE II CATALYST PROMOTED WITH IRON*

| Ex. No. | Temp. (C°) | Pressure | Catalyst Time on Stream w/o Regeneration | Contact Time (Sec.) | Mole Ratio $O_2$/DMN | Mole Ratio $NH_3$/DMN | % Conv. | Combined Nitrile Selectivity |
|---|---|---|---|---|---|---|---|---|
| 1 | 400 | 1 Atm. | 1.0 | 2.0 | 2.4 | 20.0 | 45 | 98.5 |
| 2 | 400 | 1 Atm. | 3.0 | 2.0 | 2.9 | 18.3 | 29 | 95.8 |
| 3 | 400 | 1 Atm. | 6.2 | 2.0 | 2.9 | 18.2 | 25 | 97.2 |
| 4 | 431 | 1 Atm. | 7.2 | 1.9 | 2.8 | 19.9 | 35 | 95.1 |
| 5 | 431 | 1 Atm. | 12.1 | 1.9 | 2.7 | 20.1 | 36 | 93.8 |
| 6 | 451 | 30 psig.≠ | 1.0 | 1.8 | 3.0 | 29 | 29 | 90.8 |
| 7 | 451 | 30 psig.≠ | 7.0 | 1.9 | 2.9 | 29 | 37 | 94.1 |

*Catalyst: $V_2O_5$:$Na_2O$:$Fe_2O_3$ (ca. 4:2:1); ca 15% $Fe_2O_3$; supported on α-$Al_2O_3$
≠ Run in fixed bed Stainless Steel reactor

EXAMPLES 8–12

In a series of experiments similar to the above carried out at 6 psig. the results obtained under the reaction conditions are shown in Table II.

TABLE II

AMMOXIDATION OF 2,6-DMN
CATALYST: 5 Wt. % Sodium Vanadium Bronze containing 25 Mole % $Fe_2O_3$
CONTACT TIME: 2.3 to 2.5 Seconds
PRESSURE: 6 PSIG.

| Ex. No. | Temp (° C) | Catalyst on Stream Time w/o Regeneration (Hrs). | Mole Ratio $O_2$/DMN | Mole Ratio $NH_3$/DMN | % Selectivity |
|---|---|---|---|---|---|
| 8 | 403 | 28.7 | 2.4 | 9.7 | 92.8 |
| 9 | 403 | 27.8 | 3.0 | 14.6 | 95.2 |
| 10 | 403 | 15.4 | 2.6 | 18.9 | 97.4 |
| 11 | 402 | 10.6 | 2.6 | 26.2 | 97.5 |
| 12 | 448 | 36.3 | 2.3 | 21.2 | 97.6 |

The data shown in Table III represents the average selectivity, conversion and plant yield of a series of runs made with and without the iron promoter. As can be seen from the results shown in the table, the iron does give an improvement which in plant operations would be of significant value.

TABLE III 2,6-DMN AMMOXIDATION WITH $Fe_2O_3$ MODIFIED SODIUM VANADIUM BRONZE CATALYST VERSUS UNMODIFIED BRONZES

Temperature: 450°C. Pressure: 30 Psig. (Stainless Steel Reactor)
Mole Ratio $NH_3$:DMN: 29:1 Mole Ratio $O_2$:DMN = 3:1

| Catalyst | (Average) Selectivity (%) | (Average) Conversion (%) | (Average) Plant Yield (*%) |
| --- | --- | --- | --- |
| Sodium-vanadium 8 Wt. % Bronze + 15 mole % $Fe_2O_3$ | 92.3 | 33.5 | 87.5 |
| Sodium-vanadium 8% (wt.) Bronze + 5 mole % $Fe_2O_3$ | 91 | 36 | 85 |
| Sodium-vanadium 8 Wt. % Bronze (No added $Fe_2O_3$) | 89.5 | 30 | 83.4 |

*% Plant Yield = $\frac{\text{Terephthalonitrile Out}}{\text{Fresh p-xylene in}} \times 100$

The invention claimed is:

1. An ammoxidation process for preparing 2,6-dicyanonaphthalene from 2,6-dimethylnaphthalene which comprises reacting said dimethylnaphthalene and ammonia at a temperature of from about 375° to about 550° C. in the presence of added oxygen, the molar ratio of ammonia to dimethylnaphthalene being from at least about 10:1 to about 30:1 and the catalyst for said reaction comprising at least about 0.5 to 20% by weight of an alkali metal vanadium bronze supported on α-alumina and promoted with an iron compound in an amount from about 0.5 mole percent to about 25 mole percent of the catalyst expressed as oxides.

2. An ammoxidation process for preparing 2,6-dicyanonaphthalene from 2,6-dimethylnaphthalene which comprises reacting said dimethylnaphthalene and ammonia at a temperature of from about 400° to about 450° C. in the presence of added oxygen, the molar ratio of oxygen to dimethylnaphthalene being from about 2:1 to about 3:1, the molar ratio of ammonia to dimethylnaphthalene being from about 15:1 to about 30:1, and the catalyst for said reaction comprising at least about 0.5 to 10% by weight of an alkali metal vanadium bronze supported on α-alumina and promoted with $Fe_2O_3$ in an amount of from about 0.5 to about 15 mole percent of the catalyst expressed as oxides.

3. The process of claim 2 where the catalyst is a sodium vanadium bronze.

4. The process of claim 3 where the catalyst is predominantly BZ II or the α-prime phase.

5. The process of claim 3 operated in a fixed bed mode at a pressure of from about 15 to about 50 psig.

6. The process of claim 5 where the catalyst is predominantly BZ II.

7. The process of claim 5 where the catalyst is predominantly the α-prime phase.

8. The process of claim 5 where the catalyst is a mixture of BZ II and the α-prime phase.

9. The process of claim 2 operated in a fluidized bed mode at 1 to about 5 atmospheres and the catalyst is a sodium vanadium bronze.

10. The process of claim 9 where the catalyst is predominantly BZ II.

11. The process of claim 10 where the catalyst is predominantly the α-prime phase.

12. The process of claim 10 where the catalyst is a mixture of BZ II and the α-prime phase.

* * * * *